United States Patent [19]
Mulder et al.

[11] Patent Number: 5,992,231
[45] Date of Patent: Nov. 30, 1999

[54] APPARATUS FOR MEASURING THE QUALITY OF A FLUID IN A VESSEL

[75] Inventors: Richard Mulder, Capelle a/d Ijssel; Comelis W. P. Schoenmakers, Rotterdam; Marian J. W. Slezak, Rijsbergen, all of Netherlands

[73] Assignee: Meridian Instruments B.V., Netherlands

[21] Appl. No.: 09/031,690

[22] Filed: Feb. 27, 1998

[51] Int. Cl.[6] .................................................. G01F 23/26
[52] U.S. Cl. ...................................... 73/304 C; 73/304 R
[58] Field of Search ........................... 73/861.08, 861.11, 73/861.12, 861.14, 861.16, 304 R, 304 C

[56] References Cited

U.S. PATENT DOCUMENTS

| | | | |
|---|---|---|---|
| 4,551,785 | 11/1985 | Kroner | 73/304 C |
| 4,757,252 | 7/1988 | Maltby et al. | 324/620 |
| 4,806,847 | 2/1989 | Atherton et al. | 73/304 C |
| 5,391,839 | 2/1995 | Lang et al. | 73/304 C |
| 5,546,005 | 8/1996 | Rauchwerger | 73/304 C |

FOREIGN PATENT DOCUMENTS

| | | |
|---|---|---|
| 1279204 | 6/1972 | United Kingdom . |
| 92/22808 | 12/1992 | WIPO . |
| 96/24823 | 8/1996 | WIPO . |

*Primary Examiner*—Max Noori
*Attorney, Agent, or Firm*—Banner & Witcoff, Ltd.

[57] ABSTRACT

The invention relates to an apparatus for determining the condition of a fluid in a space, comprising: a measuring electrode extending inside the space; a second electrode placed in the space; and a measuring circuit for measuring the impedance between the measuring electrode and the second electrode and calculating the condition from the impedance, wherein the measuring electrode extends at least partially uncovered in the space.

According to a preferred embodiment the apparatus is therefore provided with a measuring circuit which is adapted to measure the ohmic impedance between the measuring electrode and the auxiliary electrode. As stated, this provides the option of measuring the impedance of the substance present in the vessel so that with determined material properties it is possible to arrive at a better and more accurate measurement result.

It is pointed out herein that the present electrode also enables determining of the capacity between electrode and second electrode.

20 Claims, 4 Drawing Sheets

APPARATUS FOR MEASURING THE QUALITY OF A FLUID IN A VESSEL

BACKGROUND OF THE INVENTION

The present invention relates to an apparatus for determining the condition of a fluid in a space, comprising:

a measuring electrode extending inside the space;

a second electrode placed in the space; and a measuring circuit for measuring the impedance between the measuring electrode and the second electrode and calculating the condition of the fluid from the impedance.

Such an apparatus is known from WO 96/24823.

This known apparatus provides excellent results in measuring the quality, such as the degree of filling or the dielectric constant, of the fluid situated in the vessel. Fluid is herein understood to mean not only a gas or a liquid but also ocher substances behaving as a fluid, such as granulates and substances in powder form.

This known apparatus measures not only the capacity between the measuring electrode and the second electrode but also the ohmic resistance connected in parallel thereto, or the conductivity of the product between the measuring electrode and the second electrode. It will be apparent that the measurement result is influenced hereby.

There is therefore a need for an apparatus for measuring substances by means of other properties, such as the ohmic resistance. This is for instance also the case with substances wherein the dielectric constant differs only little from that of air.

This known apparatus moreover has the drawback that when the dielectric constant of the substance present in the space is not known precisely, the measurement signal is a function of the dielectric constant of the substance and of the degree of filling.

It is of course possible to arrange a separate measuring electrode for this purpose which is always immersed in the substance and which serves to compensate the dielectric constant, although this results in a costly and thus less attractive solution.

BRIEF DESCRIPTION OF THE INVENTION

The object of the present invention is therefore to provide such an apparatus which offers more possibilities for measuring electrical properties of the substance present in the space.

This object is achieved in that a measuring electrode extends at least partially uncovered in the space.

It is pointed out here that the apparatus known from WO 96/24823 is always provided with an electrode provided with an external protective layer. It is thus not possible herewith to measure for instance the ohmic resistance of the substance present in the vessel, since the ohmic resistance of the protective material is usually so high that the resistance of the material connected thereto in series is hardly measurable and certainly cannot result in measurement signals of the required accuracy.

The apparatus according to the invention can be applied in a space which is bounded by a vessel, wherein the second electrode is formed by at least one conductive part of the vessel wall.

The apparatus according to the invention can also be applied in a space wherein the second electrode is formed by earth or by an auxiliary electrode extending around the measuring electrode.

According to a preferred embodiment the apparatus is therefore provided with a measuring circuit which is adapted to measure the ohmic impedance between the measuring electrode and the auxiliary electrode. As stated, this provides the option of measuring the impedance of the substance present in the vessel so that with determined material properties it is possible to arrive at a better and more accurate measuring result.

It is pointed out herein that the present electrode also enables determining of the capacity between electrode and second electrode. With such an apparatus it is thus possible on the one hand to choose the most suitable measuring method, while the option is provided on the other to use both measuring methods alternately.

For such a situation it is only necessary that the uncovered part of the measuring electrode extends over only a part of the height of the space. It is then only necessary to establish whether the quality of the fluid lies below or above a predetermined threshold value.

The electrode is preferably received in a support, wherein the measuring electrode is separated from the earthed parts of the vessel wall by a compensation electrode which is connected to the compensation circuit. This relates to the measure already known per se from the above mentioned international patent application, but the use of which in measuring the ohmic resistance is new.

According to yet another preferred embodiment the compensation electrode has a mechanically supporting function and the measuring electrode is connected to the compensation electrode by means of an insulating connecting element, wherein an electrical connection between the measuring electrode and the measuring circuit extends through the compensation electrode embodied in hollow form.

In some situations it is desirable to determine whether the level of the material in the vessel lies below or above a determined threshold value. This is for instance important in particular process controls or it may be important in safety measures.

Other attractive preferred embodiments are to be found in the remaining sub-claims.

BRIEF DESCRIPTION OF THE DRAWINGS

The present invention will elucidated hereinbelow with reference to the annexed drawings, in which.

DETAILED DESCRIPTION OF THE INVENTION

Figure 1:
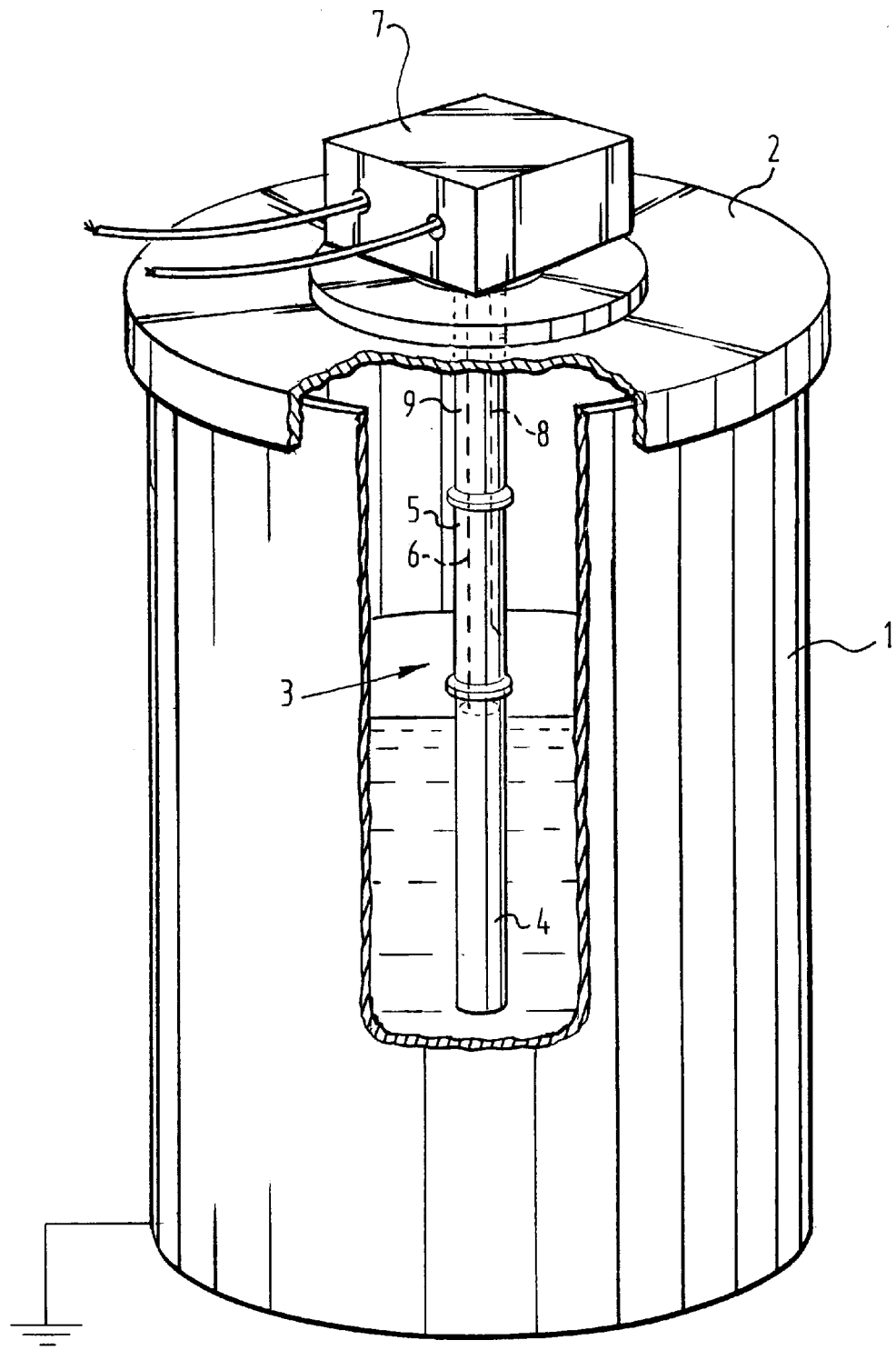
FIG. 1 shows a partly broken away perspective view of a vessel in which is arranged an apparatus according to the present invention.

FIG. 1 shows a vessel 1 which is manufactured from conductive material and on which is placed a cover 2. Arranged in the cover is an electrode 3 which is formed by an actual measuring electrode 4 and a guard electrode 5. The compensation electrode 5 takes a hollow form and an electrical connection 6 extends through compensation electrode 5 to a junction box 7 arranged on top of the cover. The compensation electrode embodied in hollow form is connected to the junction box with a connection 8. Arranged around the connections 6, 8 is a further guard electrode 9 which is connected to the rest of housing 1, in particular to cover 2. The whole assembly of vessel 1, cover 2 and electrode 9 is earthed. A possible cathodic protection device is herein omitted. Even if such a cathodic protection device is present, the entire above mentioned assembly is deemed as earthed in respect of the measuring system.

As stated, the actual measuring electrode 4 is not provided with a protective layer as is the case in the prior art measuring apparatus. This has the consequence that, as in the prior art, the electrode can be used to measure the capacity between vessel wall and electrode, but also to measure the ohmic resistance between vessel wall and electrode. The advantages hereof have been pointed out in the description introduction.

It is noted here that the protective layer of insulating material usually had the function of protecting the electrode against aggressive substances accommodated in the vessel and to prevent so-called "adhesion" of granulate-type substances to the electrode as the vessel empties.

It is noted here that these problems occurred particularly at the transitions between the actual measuring electrode and the compensation electrode and between the compensation electrode and the earthed part of the vessel. These problems are avoided by applying specific constructions.

Such a construction will be elucidated below with reference to FIG. 2.

Figure 2:
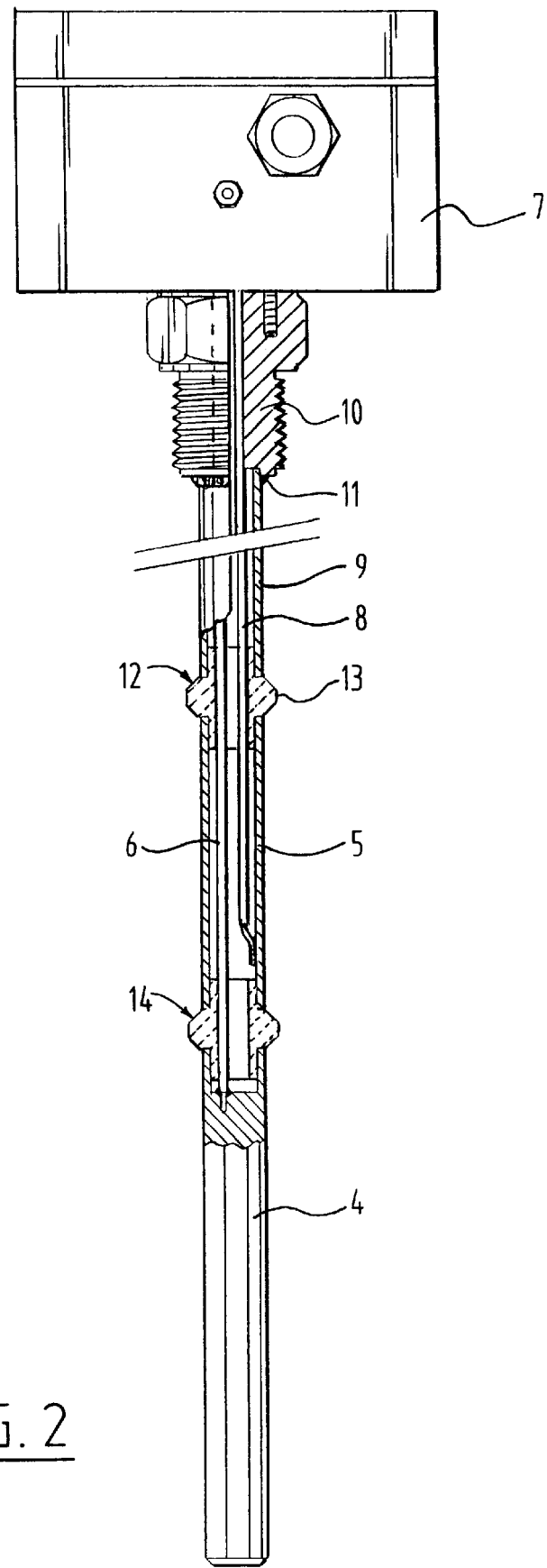
FIG. 2 shows a view partially in cross-section of an electrode for use in the apparatus according to the present invention.

FIG. 2 shows the electrode 3 in its entirety, wherein the whole assembly of measuring electrode 4, compensation electrode 5 and guard electrode 9 is connected over a lead-through 10 to the box 7. It will be apparent that lead-through 10 takes a hollow form, since connections 6 and 8 must extend therethrough to the box 7. Lead-through 10 is generally embodied in conductive material and is connected to guard electrode 9 by means of for instance a weld connection 11. Compensation electrode 5 must of course be deployed in electrically insulating manner relative to the guard electrode 9. Use is made for this purpose of a coupling piece 12 which in the present embodiment is embodied in ceramic material. Such coupling pieces of ceramic material are provided with a rail 13 to prevent bridge formation of powder or granular material or of liquids at a potential transition between guard electrode 9 and compensation electrode 5. For fixing of both electrodes 9 respectively 5 to coupling piece 12 use can be made of different techniques; it is thus possible to make use of a soldering technique which has been available since recently and which enables solder connections to be made between ceramic materials and metal. It is further possible to make use of a clamping or shrunk connection, while it is finally possible to make use of glue connections Other methods of connection are however in no way excluded.

A similar consideration applies for the connecting piece 14 arranged between compensation electrode 5 and the actual measuring electrode 4. The same methods of connection can also be used here.

It is pointed out that the invention is not limited by the use of ceramic coupling pieces; it is equally possible to make use of coupling pieces of other types of material, for instance plastics.

What is essential however is that they have a required mechanical robustness, can withstand many substances and provide sufficient mechanical strength.

It is also noted here that in the present embodiment the measuring electrode 4 extends over only a short length. This is related to a specific application of the present invention, wherein all that is determined is whether a quality of the substance lies below or above a determined point; an example hereof is whether or not the degree of filling of the vessel with a particular substance has exceeded a determined threshold value. Such an apparatus can also be used to measure the dielectric constant, respectively the resistance of a determined material. Such a measurement may be of significance for instance in process controls.

The present invention is however in no way limited thereto; it is very well possible for instance, though not necessary, to generate a signal with a longer measuring electrode, a property of which signal represents a quality of the substance present in the vessel.

Nor is the invention limited to the shown electrode configuration; it is possible to make use of earth as second electrode; the measuring circuit then measures against earth.

Figure 3:
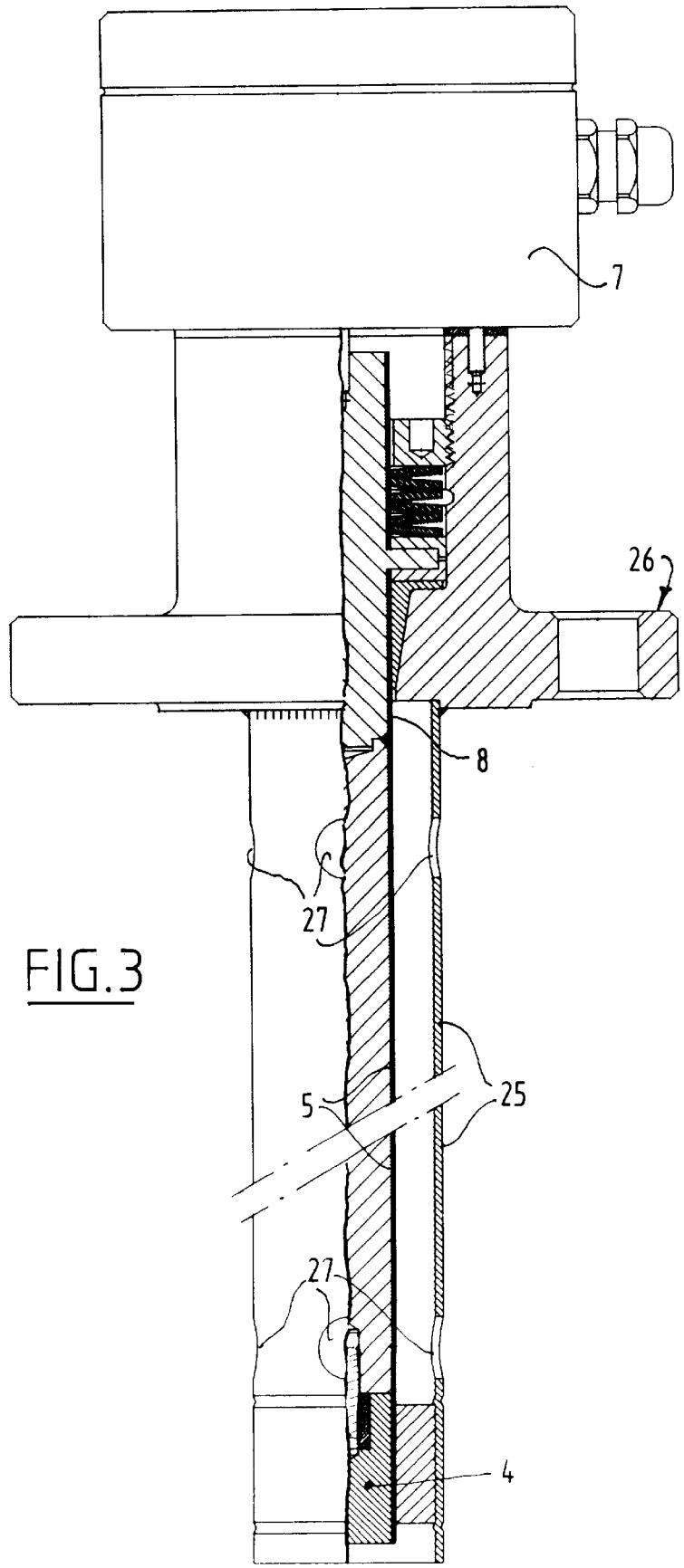
FIG. 3 shows a view partially in cross-section of a variant of an electrode with an auxiliary electrode according to the invention.

According to yet another embodiment use is made of an auxiliary electrode as second electrode. Such an embodiment is shown in FIG. 3.

An auxiliary electrode 25 in the form of a hollow cylinder is herein arranged round the electrode 3. This hollow cylinder 25 is manufactured from conductive material and is connected to earth in the drawn embodiment with a flange 26.

Holes 27 are arranged in hollow cylinder 25. These holes serve to cause the level of the material in the space between electrode 3 and hollow cylinder 25 to be as far as possible the same as the level of the fluid in the space outside the hollow cylinder. This is in any case essential for performing a measurement as representative as possible of the actual level. The presence of the material in question in the space between the electrode and the hollow cylinder is of course also important for measuring the properties of the fluid.

The most important function of the hollow cylinder is to make smaller the distance between the measuring electrode and the second electrode. This provides the option of performing a reliable measurement within the measuring range of the apparatus even in the case of high values of the specific electrical resistance or of low values of the dielectric constant of the fluid.

A secondary function lies in the mechanical protection of the actual measuring electrode, particularly but not exclusively in flowing fluids.

The above stated embodiments all have a measuring electrode body which is rigidly mounted on the vessel or the cover of the vessel. It is also possible however to suspend the electrode body from a cable. Only the actual measuring electrode need herein be suspended; in respect of the large distance between vessel wall and measuring electrode, the compensation electrode can be omitted.

Figure 4:
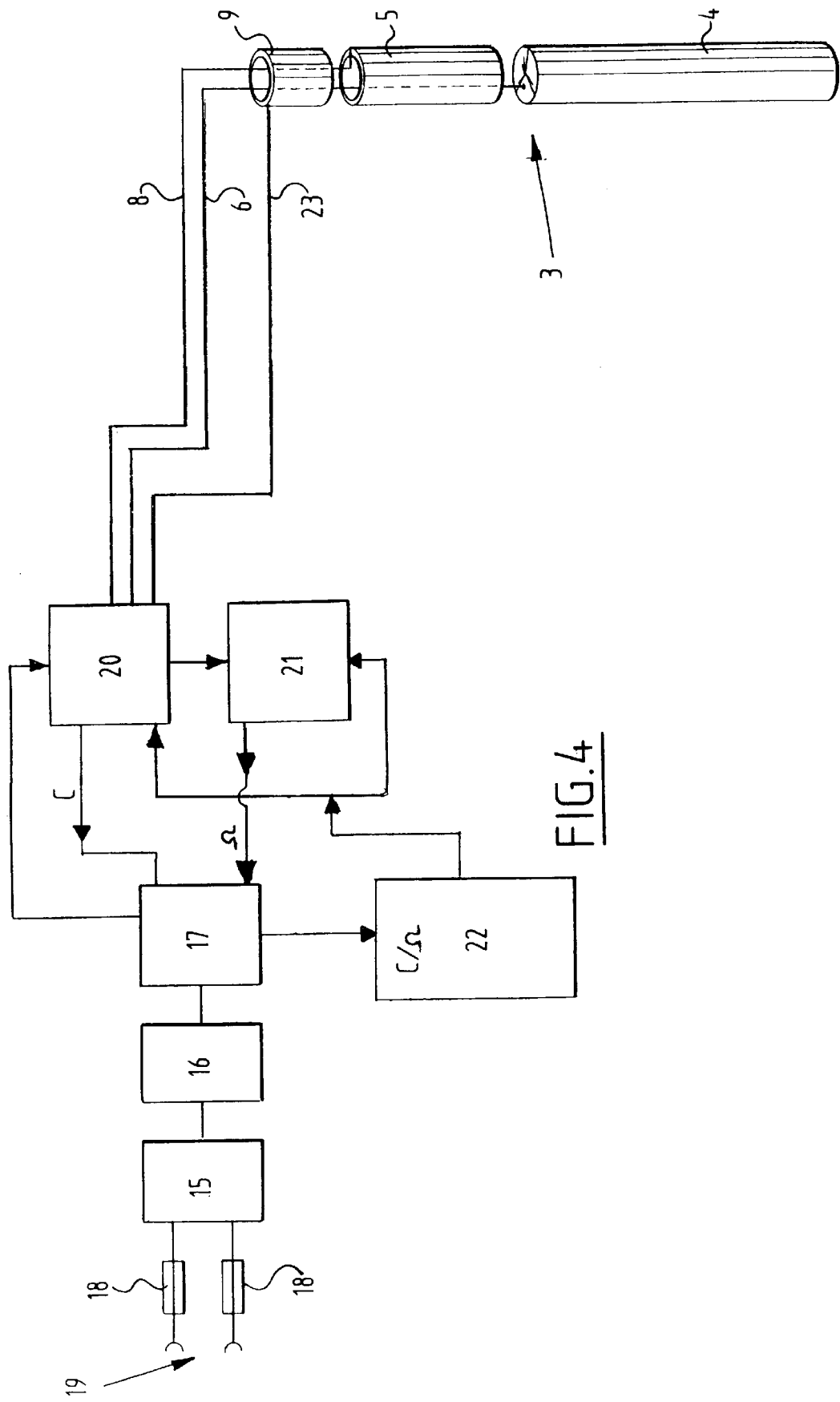
FIG. 4 shows a diagram of the electrical circuit according to the present invention.

An embodiment of the circuit required for performing the measurements is shown schematically in FIG. 4. Use is made herein of a circuit which is accommodated for instance in the junction box 7; it is very well possible however for the measuring circuit to be situated at a different point.

The circuit essentially comprises a safety circuit 15, a power supply and conversion circuit 16 and a microprocessor 17. It is pointed out herein that safety circuit 15 is connected to the supply connections 19 by means of two melting electrodes 18. The melting fuses 18 are in any case necessary because this is a compulsory directive of safety regulations in a large number of countries. In the case of failure of such a melting fuse, which is usually arranged in the circuit at very inaccessible locations, being for instance moulded therein,. the whole circuit must be removed. In order to prevent these problems an electronic safety circuit 15 is applied which already responds at a lower level of current respectively voltage, hereby protecting the circuit and avoiding melting through of fuses 18.

The power supply circuit 16 serves to convert the supply signal to a value with which microprocessor 17 and the other circuits can be supplied.

Such a circuit is in principle already described in the above mentioned patent application with publication number WO 96/24823.

The apparatus subsequently comprises a measuring circuit 20 for measuring the capacity and for measuring the ohmic resistance. Measuring circuit 20 for measuring the capacity has in essence already been described. A measuring circuit for measuring the capacity is already discussed in the above mentioned international patent publication. For measuring the ohmic resistance use is made of the same circuit 20, which can also be provided with for instance a classic measuring bridge. It is herein possible to apply numerous measuring principles which will all be clear to skilled persons. It is noted herein that the measuring circuit is thus suitable for alternately performing both measuring functions, i.e. measuring of the capacity between the electrodes and measuring of the resistance between the electrodes. The measuring apparatus further comprises an auxiliary circuit 21 which converts the signal received from measuring circuit 20 into a signal representing the ohmic resistance.

Both measuring circuits 20 and 21 are controlled by the selector circuit 22 which can cause measuring circuit 20 to measure the ohmic resistance or the capacity.

It is pointed out herein that measuring electrode 4, compensation electrode 5 and earth electrode 9 are connected to measuring circuit 20. Use is made herein of an earth connection 23.

It will be apparent that it is possible with the thus shown apparatus to measure both the capacity and the ohmic resistance.

In some situations it will not be necessary to measure both quantities; the relevant part of the circuit can then be omitted. In other situations it is attractive to measure both elements; to this end the microprocessor 17 can be programmed such that measuring circuit 20 alternately measures ohmic resistance and capacity. The measurement signals resulting herefrom can then be processed in microprocessor 17 and converted into associated information signals which can be transmitted via supply lines 19 to the central processing circuit not shown in the drawing.

It is noted here that said diagram only shows the circuit very schematically; it will be apparent that the circuit is embodied in much greater detail; the professional knowledge required for this purpose will however be known to the skilled person concerned.

It is further pointed out that between microprocessor 17 and measuring circuits 20, 21 and 22 there is of course a galvanic separation present in order to obtain a necessary galvanic separation between the earthed vessel and the other measurement signals. This galvanic separation can otherwise also be arranged at other locations in the circuit.

It is finally noted that it is of course possible to omit unused components from these circuits.

We claim:

1. Apparatus for determining the condition of a fluid in a space, comprising:
   a measuring electrode extending inside the space;
   a second electrode placed in the space; and
   a measuring circuit for measuring the impedance between the measuring electrode and the second electrode and calculating the condition from the impedance,
   characterized in that the measuring electrode extends at least partially uncovered in the space.

2. Apparatus as claimed in claim 1, characterized in that the space is a vessel and the second electrode is formed by at least one conductive part of the vessel wall.

3. Apparatus as claimed in claim 1, characterized in that the second electrode is formed by earth.

4. Apparatus as claimed in claim 1, characterized in that the second electrode is formed by an auxiliary electrode surrounding the measuring electrode.

5. Apparatus as claimed in any of the claim 1, characterized in that the measuring circuit is adapted to measure the ohmic impedance between the measuring electrode and the second electrode.

6. Apparatus as claimed in claim 2, characterized in that the uncovered part of the measuring electrode extends over only a part of the height of the vessel.

7. Apparatus as claimed in claim 6, characterized in that the electrode is received in a support, wherein the measuring electrode is separated from earthed parts of the vessel wall by a compensation electrode which is connected to a compensation circuit.

8. Apparatus as claimed in claim 7, characterized in that the compensation electrode has a mechanically supporting function, the measuring electrode is connected to the compensation electrode by means of an insulating connecting element, and an electrical connection between the measuring electrode and the measuring circuit extends through the compensation electrode embodied in hollow form.

9. Apparatus as claimed in claim 8, characterized in that the compensation electrode is connected to the vessel wall by means of an insulating connecting element and a hollow earth electrode having a supporting function.

10. Apparatus as claimed in claim 8, characterized in that the connecting element is manufactured from ceramic material.

11. Apparatus as claimed in claim 9, characterized in that the measuring electrode and the compensation electrode are connected to the connecting element by means of soldering.

12. Apparatus as claimed in claim 9, characterized in that the electrodes are connected to the connecting element by means of a shrunk connection.

13. Apparatus as claimed in claim 1, characterized in that the measuring circuit is adapted to establish whether the quality of the fluid lies below or above a predetermined threshold value.

14. Apparatus as claimed in claim 1, characterized in that the measuring circuit is adapted to also measure the capacity between the measuring electrode and the second electrode.

15. Apparatus as claimed in claim 14, characterized in that the measuring circuit is adapted to alternately measure the capacity and the ohmic resistance and to calculate therefrom the quality of the fluid.

16. Apparatus as claimed in claim 1, characterized in that the electrode is connected to the measuring circuit by means of a cable and that between the measuring circuit and the cable is arranged an additional, electronically embodied safety circuit.

17. Apparatus as claimed in claim 16, characterized in that the safety circuit is adapted to respond to values which are lower than the response values of the thermally embodied safety elements present in accordance with safety regulations.

18. Apparatus as claimed in claim 4, characterized in that the uncovered part of the measuring electrode extends over only a part of the height of the vessel.

19. Apparatus as claimed in claim 9, characterized in that the connecting element is manufactured from ceramic material.

20. Apparatus as claimed in claim 10, characterized in that the measuring electrode and the compensation electrode are connected to the connecting element by means of soldering.

* * * * *